United States Patent
Oh et al.

(10) Patent No.: US 9,157,845 B2
(45) Date of Patent: Oct. 13, 2015

(54) 2-D MEMS TRIBOMETER WITH COMB DRIVES

(75) Inventors: Yunje Oh, Medina, MN (US); Syed Amanula Syed Asif, Bloomington, MN (US); Oden L. Warren, New Brighton, MN (US)

(73) Assignee: Hysitron Incorporated, Minneapolis, MN (US)

( * ) Notice: Subject to any disclaimer, the term of this patent is extended or adjusted under 35 U.S.C. 154(b) by 1199 days.

(21) Appl. No.: 13/099,113

(22) Filed: May 2, 2011

(65) Prior Publication Data

US 2011/0265559 A1 Nov. 3, 2011

Related U.S. Application Data

(60) Provisional application No. 61/330,120, filed on Apr. 30, 2010.

(51) Int. Cl.
G01N 3/42 (2006.01)
B82Y 35/00 (2011.01)
G01Q 60/36 (2010.01)

(52) U.S. Cl.
CPC . G01N 3/42 (2013.01); B82Y 35/00 (2013.01); G01Q 60/366 (2013.01); *G01N 2203/0286* (2013.01)

(58) Field of Classification Search
CPC ............ G01N 2203/0286; G01N 3/42; G01N 2203/0051; G01N 3/40; G01N 2203/005; G01N 19/00; G01N 3/46; B82Y 35/00; G01Q 60/366; G01Q 10/04; G01Q 10/02; G01Q 60/38; G01Q 60/16; G01Q 60/22; G01Q 70/02; G01Q 70/06; Y10S 977/956; G01B 7/34
USPC .................. 73/78–85, 105; 250/311; 977/956
See application file for complete search history.

(56) References Cited

U.S. PATENT DOCUMENTS 5,553,486 A 9/1996 Bonin (Continued)

FOREIGN PATENT DOCUMENTS

| JP | 2000-501842 | 2/2000 |
|---|---|---|
| WO | 0218905 | 3/2002 |
| WO | 2010003149 | 1/2010 |

OTHER PUBLICATIONS

Desai et al., A novel MEMS nano-tribometer for dynamic testing in-situ in SEM and TEM, Tribology Letters, vol. 18, No. 1, Jan. 2005, pp. 13-19.

(Continued)

*Primary Examiner* — Daniel S Larkin
*Assistant Examiner* — Jamar Ray
(74) *Attorney, Agent, or Firm* — Dicke, Billig & Czaja, PLLC

(57) ABSTRACT

A microelectromechanical (MEMS) nanoindenter transducer including a body, a probe coupled to and moveable relative to the body, the probe holding a removeable indenter tip, a first micromachined comb drive and a second micromachined comb drive. The first micromachined comb drive includes an actuator comprising a plurality of electrostatic capacitive actuators configured to drive the probe along a first axis, including in an indentation direction, in response to an applied bias voltage, and a displacement sensor comprising a plurality of differential capacitive sensors having capacitance levels which together are representative of a position of the probe relative to the first axis. The second micromachined comb drive includes an actuator comprising a plurality of electrostatic capacitive actuators configured to drive the probe along a second axis, which is perpendicular to the first axis, in response to an applied bias voltage, and a displacement sensor comprising a plurality of differential capacitive sensors having capacitance levels which together are representative of a position of the probe relative to the second axis. Each of the electrostatic capacitive actuators and the differential capacitive sensors comprises an electrode comb pair, each electrode comb pair including a fixed electrode comb coupled to the body and a moveable electrode comb coupled to the probe.

15 Claims, 13 Drawing Sheets

(56) References Cited

U.S. PATENT DOCUMENTS

| | | | |
|---|---|---|---|
| 5,661,235 A | 8/1997 | Bonin | |
| 5,801,472 A | 9/1998 | Wada et al. | |
| 5,869,751 A * | 2/1999 | Bonin | 73/105 |
| 6,520,004 B1 | 2/2003 | Lin | |
| 6,640,459 B1 | 11/2003 | Lucas et al. | |
| 2004/0011119 A1 | 1/2004 | Jardret et al. | |
| 2006/0137469 A1 | 6/2006 | Yang et al. | |
| 2006/0191327 A1 | 8/2006 | Yang et al. | |
| 2010/0036636 A1 * | 2/2010 | Oh et al. | 702/113 |
| 2010/0100990 A1 * | 4/2010 | Trumper et al. | 850/8 |

OTHER PUBLICATIONS

Search Report, PCT, Jul. 13, 2012, 11 pages.

* cited by examiner

TABLE I

| PARAMETER | NORMAL MOTION (Z-AXIS) | LATERAL MOTION (X-AXIS) |
|---|---|---|
| OVERLAPPING ELECTRODE AREA | 0.156 mm$^2$ | 0.085 mm$^2$ |
| NOMINAL ELECTRODE GAP | 10 μm | 10 μm |
| PULL-IN VOLTAGE | 217 V | 261 V |
| PULL-IN DISTANCE | 3.33 μm | 3.33 μm |
| BREAK DOWN VOLTAGE AT NOMINAL GAP | 306 V | 306 V |
| ELECTROSTATIC FORCE CONSTANT AT NOMINAL GAP | 6.91 nN/V$^2$ | 3.74 nN/V$^2$ |
| MAXIMUM ELECTROSTATIC FORCE AT NOMINAL GAP | 552 μN | 299 μN |
| TRAVEL LIMIT | 3 μm (HARDWARE) 1 μm (SOFTWARE) | 3 μm (HARDWARE) 1 μm (SOFTWARE) |

Fig. 6

TABLE II

| PARAMETER | NORMAL MOTION (Z-AXIS) | LATERAL MOTION (X-AXIS) |
| --- | --- | --- |
| OVERLAPPING ELECTRODE AREA | 0.528 mm$^2$ | 0.231 mm$^2$ |
| NOMINAL ELECTRODE GAP | 6 μm | 6 μm |
| NOMINAL CAPACITANCE | 779 fF | 341 fF |
| DISPLACEMENT SENSITIVITY AT NOMINAL ELECTRODE GAP | 64.9 fF/μm | 28.4 fF/μm |
| FORCE SENSITIVITY AT NOMINAL ELECTRODE GAP | 0.293 fF/μN | 0.164 fF/μN |
| NONLINEARITY | 0.16% IN FULL SCALE (WITHIN 1 μm) | 0.21 IN FULL SCALE (WITHIN 1 μm) |

Fig. 8

TABLE III

| PARAMETER | NORMAL MOTION (Z-AXIS) | LATERAL MOTION (X-AXIS) |
|---|---|---|
| STIFFNESS | 219 N/m | 173 N/m |
| DISPLACEMENT NOISE IN QUASI-STATIC OPERATION | 4.35 pm rms | 4.89 pm rms |
| FORCE NOICE IN QUASI-STATIC OPERATION | 952 pN rms | 846 pN rms |
| MAXIMUM STRESS WITH 1-μm DISPLACEMENT | 24 MPa | 20 MPa |

Fig. 10

TABLE IV

| PARAMETER | NORMAL MOTION (Z-AXIS) | LATERAL MOTION (X-AXIS) |
|---|---|---|
| RESONANCE FREQUENCY | 3.24 kHz | 4.11 kHz |
| MECHANICAL QUALITY FACTOR | 50 (AIR), 10,000 (VACUUM) | 50 (AIR), 10,000 (VACUUM) |
| DISPLACEMENT NOISE IN DYNAMIC OPERATION | 0.431 pm rms /$\sqrt{Hz}$ (AIR) 6.09 pm rms /$\sqrt{Hz}$ (VACUUM) | 0.431 pm rms /$\sqrt{Hz}$ (AIR) 6.09 pm rms /$\sqrt{Hz}$ (VACUUM) |
| FORCE NOISE IN DYNAMIC OPERATION | 1.89 pN rms /$\sqrt{Hz}$ (AIR) 0.133 pN rms /$\sqrt{Hz}$ (VACUUM) | 1.49 pN rms /$\sqrt{Hz}$ (AIR) 0.105 pN rms /$\sqrt{Hz}$ (VACUUM) |

Fig. 11

2-D MEMS TRIBOMETER WITH COMB DRIVES

CROSS-REFERENCE TO RELATED APPLICATIONS

This Utility Patent Application claims benefit of U.S. Provisional Application 61/330,120, filed Apr. 30, 2010, and which is incorporated herein by reference.

BACKGROUND

Nanoindentation is a method to quantitatively measure the mechanical properties of a test sample, such as elastic modulus and hardness, for example, using a small force and a high resolution displacement sensor. Typically, a force employed in nanoindentation is less than 10 mN, with a typical displacement range being smaller than 10 µm, and with a noise level typically being better than 1 nm rms. In nanoindentation, a nanoindenter capable of determining the loading force and displacement is used. The force and displacement data are used to determine a sample's mechanical properties. For this sample property estimation, a nanoindenter has to be integrated with a characterized tip which has known geometry and known mechanical properties. A nanoindenter with two dimensional force and displacement sensing can be used as a nano-tribometer for tribological applications for measuring additional mechanical properties such as friction and wear.

One of the key components in nanoindentation instrumentation is a transducer which converts an electrical input into a mechanical force and a mechanical displacement into an electrical signal. A well designed nanoindenter transducer can improve many aspects of the nanoindenter performance such as increasing the range of forces, including increasing the maximum force, improving force resolution and system bandwidth, and reducing system noise.

One of the emerging nanoindentation applications is quantitative in-situ nanomechanical testing within a transmission electron microscopy (TEM). This testing method enables monitoring of the deformation of a sample in real time while measuring the quantitative mechanical data. To achieve such testing capabilities, a quantitative transducer capable of applying force and measuring displacement should be integrated with a TEM holder. The physical size of the transducer is limited by the size of the TEM holder, which depends on the pole gap of the TEM. For example, TEM holders manufactured by FEI have a maximum allowable outer diameter of 4 mm, and some TEMs having smaller holder diameters, require a small transducer in order to be compatible with FEI and Hitachi TEMs.

In view of the above, the physical size of the tribometer must be reduced. The importance of making smaller tribometers is evident from TEM market data which shows FEI and JEOL each have a 40% market share, with various others having the remaining 20%. Making a smaller tribometer will enable expansion of in-situ nano-tribology testing capabilities to FEI and some other TEMs. MEMS technology is one technology which enables miniaturization the nano-tribometer without detracting from performance requirements.

A 1-Dimensional (1-D) MEMS transducer has been developed, as described by U.S. patent application Ser. No. 12/497,834, filed on Jul. 6, 2009, which is assigned to the same assignee as the present disclosure, and which is incorporated by reference herein. However, such MEMS transducer provides actuation and sensing along a single axis (i.e. 1-dimensional), that being along an axis of indentation.

SUMMARY

One embodiment provides a microelectromechanical (MEMS) nanoindenter transducer including a body, a probe coupled to and moveable relative to the body, the probe holding a removeable indenter tip, a first micromachined comb drive and a second micromachined comb drive. The first micromachined comb drive includes an actuator comprising a plurality of electrostatic capacitive actuators configured to drive the probe along a first axis, including in an indentation direction, in response to an applied bias voltage, and a displacement sensor comprising a plurality of differential capacitive sensors having capacitance levels which together are representative of a position of the probe relative to the first axis. The second micromachined comb drive includes an actuator comprising a plurality of electrostatic capacitive actuators configured to drive the probe along a second axis, which is perpendicular to the first axis, in response to an applied bias voltage, and a displacement sensor comprising a plurality of differential capacitive sensors having capacitance levels which together are representative of a position of the probe relative to the second axis. Each of the electrostatic capacitive actuators and the differential capacitive sensors comprises an electrode comb pair, each electrode comb pair including a fixed electrode comb coupled to the body and a moveable electrode comb coupled to the probe.

BRIEF DESCRIPTION OF THE DRAWINGS

FIG. 6 is a Table I illustrating a detailed performance description of electrostatic actuating capacitor, according to one embodiment.

FIG. 8 is a Table II illustrating detailed performance information of normal or Z-axis displacement capacitors, according to one embodiment.

FIG. 10 is a Table III illustrating detailed static characteristics of a 2-D MEMS transducer, according to one embodiment.

FIG. 11 is a Table IV detailing dynamic characteristics of a 2-D MEMS transducer, according to one embodiment

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

According to embodiments described herein, a micromachined comb drive is provided for performing nanoindentation tests to determine surface properties of materials. According to one embodiment, the micromachined comb drive includes an actuation comb configured as an electrostatic actuator for actuation of a moveable probe including an indenter tip and four sensing combs configured as displacement sensors to provide displacement sensing in two orthogonal directions as well as angular rotation.

Figure 1:
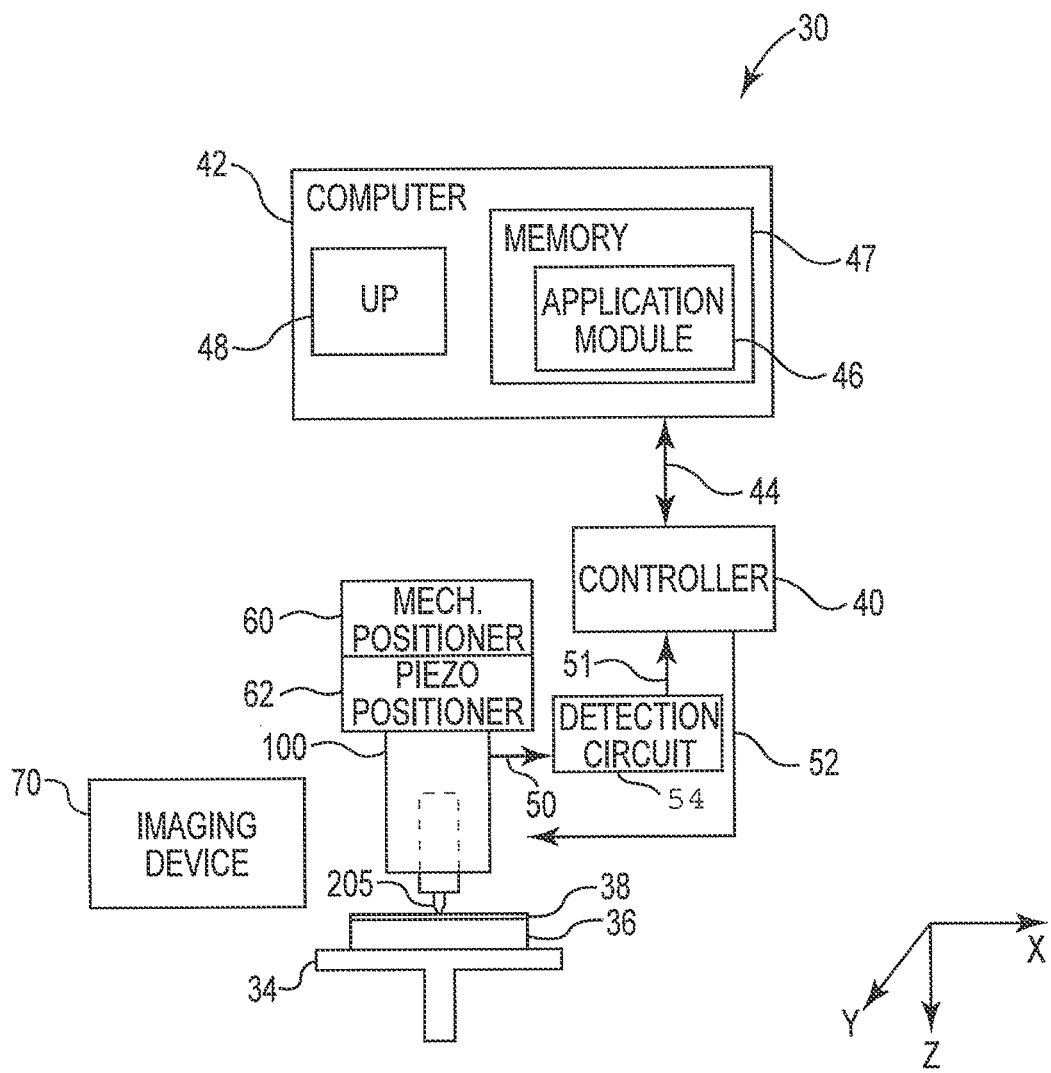
FIG. 1 is a block diagram of a nanoindentation test system employing a 2-D MEMS nanoindenter transducer according to one embodiment.

FIG. 1 is a block diagram generally illustrating one embodiment of a nanomechanical test system 30 employing a 2-D MEMS nanoindenter transducer 100 according to the present disclosure. In addition to 2-D MEMS nanoindenter transducer 100, which includes an indenter tip 205 mounted thereto, system 30 includes a platform 34 configured to hold a test sample 36 having a surface 38 to be tested via nanoindentation and nanoscratch, and a controller 40 in communication with a computer 42 via an interface 44. Test system 30 is at least suitable for in-situ sample testing.

According to one embodiment, 2-D MEMS nanoindenter transducer 100 is configured to provide to a detection circuit 54 capacitive signals 50 which are representative of a displacement of indenter tip 205 in a vertical direction (z-dimension), in orthogonal horizontal directions (x- and y-dimensions), and of rotational movement relative to platform 34. According to one embodiment, detection circuit 54 converts capacitive signals 50 to voltage signal 51. According to one embodiment, controller 40 converts voltage signal 51 to digital signals and provides the digital signals to computer 42 via interface 44. According to one embodiment, based on these digital signals, an application module 46 (e.g. software) provides a digital actuation signal to controller 40 which, in-turn, converts the digital actuation signal to an actuation voltage signal 52 which is provided to micromachined comb drive 100 so as to actuate or displace indenter tip 205 a desired distance along the z-axis relative to platform 34.

According to one embodiment, controller 40, via application module 46 of computer 42, is configured to control movement of indenter tip 205 relative to platform 34 and to provide to computer 42 via interface 44 a signal representative of a displacement of indenter tip 205 from an initial reference point. According to one embodiment, controller 40 is configured to measure and adjust the actuation force.

According to one embodiment, application module 46 comprises instructions stored in a memory system 47 that are accessible and executable by a processor 48. Memory system 47 may comprise any number of types of volatile and non-volatile storage devices such as RAM, hard disk drives, CD-ROM drives, and DVD drives. In other embodiments, application module 46 may comprise any combination of hardware, firmware, and software components configured to perform at least the functions described herein.

According to one embodiment, nanomechanical test system 30 includes a mechanical positioner 60 and a piezo positioner 62 which enable 3-D positioning of 2-D nanoindenter transducer 100 and indenter tip 205 coupled thereto. In one embodiment, initial positioning of nanoindenter transducer 100 and indenter tip 205 is performed via mechanical positioner 60 and piezo positioner 62, and final positioning and movement of indenter tip 205 is performed via nanoindenter transducer 100.

According to one embodiment, nanomechanical test system 30 further includes an imaging device 70 which provides viewing of surface 38 of test sample 36. According to one embodiment, imaging device 70 comprises an instrument/device capable of recording or determining the profile or contour of a test region such as, for example, an optical microscope, a profilometer, a scanning probe microscope (SPM), or an atomic force microscope (AFM), which is configured to provide images of surface 38 of sample 36.

Examples of systems similar to test apparatus 30 and suitable to be configured for use with the micromachined comb drive and indenter tip according to the present disclosure are described by U.S. Pat. Nos. 5,553,486 and 5,869,751, both of which are assigned to the same assignee as the present disclosure and incorporated herein by reference. Another test system suitable to be configured for use with the micromachined comb drive and indenter tip according to the present disclosure is commercially available under the tradename TriboIndenter from Hysitron, Incorporated, of Minneapolis, Minn., USA.

Figure 2:
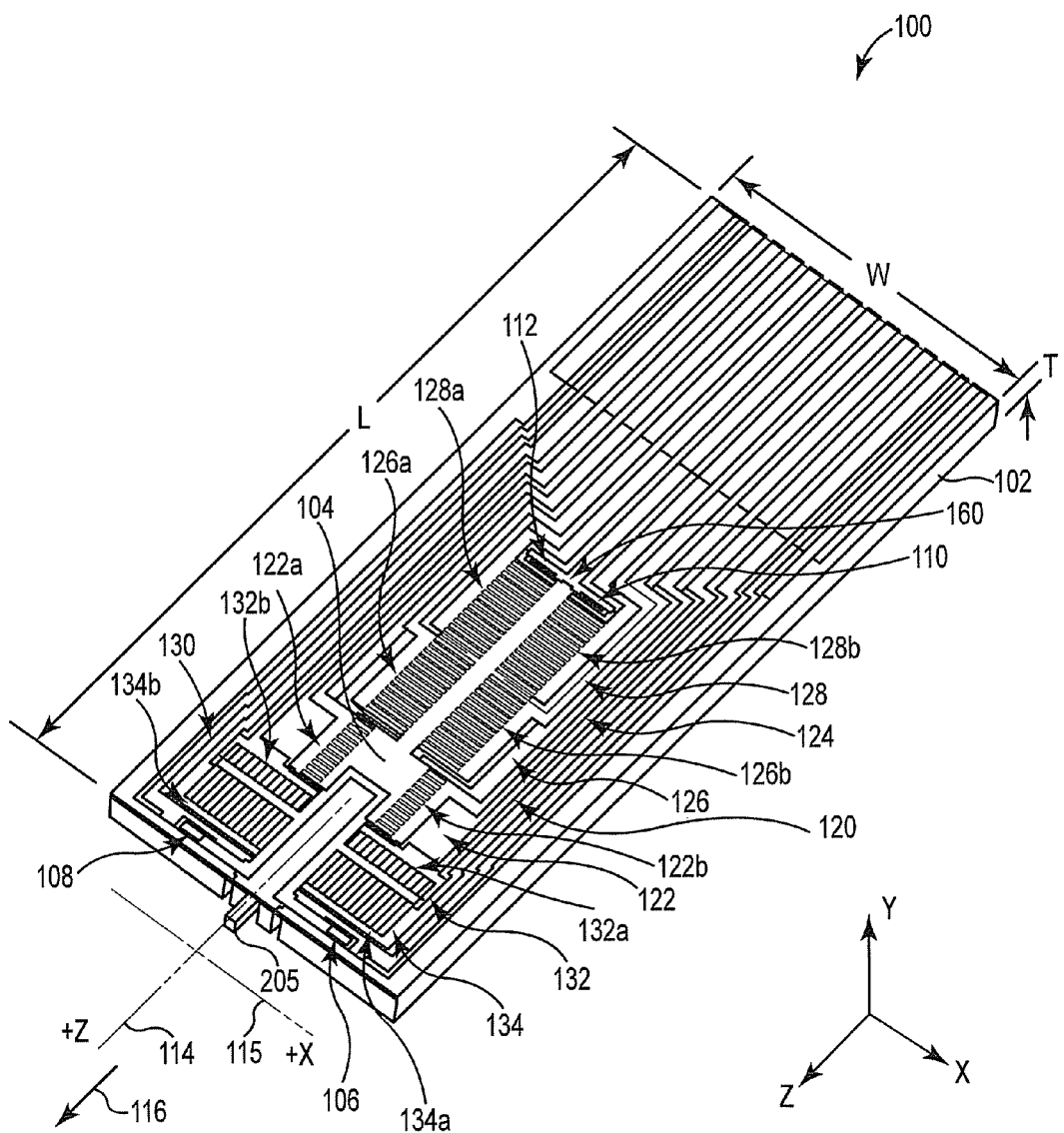
FIG. 2 is a perspective of 2-D MEMS nanoindenter transducer according to one embodiment.

FIG. 2 is a perspective view illustrating 2-D MEMS nanoindenter transducer 100, according to one embodiment of the present disclosure, and which illustrates removable indenter tip 205 as being mounted to 2-D MEMS nanoindenter transducer 100. According to one embodiment, 2-D MEMS nanoindenter transducer 100 includes a body 102 and a moveable probe 104 which is supported from body 102 by a pair of front springs 106, 108 and a pair of rear springs 110, 112. The springs are formed in a fashion such that moveable probe 104 is more readily displaceable along a Z-axis 114 (referred to as the displacement axis), including in an indentation direction 116 (the +Z direction in FIG. 1), than in other directions, such as along the X-axis 115.

2-D MEMS nanoindenter transducer 100 further includes a first, or Z-axis, micromachined comb drive 120 (also referred to as the normal comb drive), and a second, or X-axis, micromachined comb drive 130 (also referred to as the lateral comb drive). First micromachined comb drive 120 includes an actuation capacitor 122 (referred to as a Z-axis actuator) formed by first and second actuation capacitor 122a and 122b, and a displacement sensor capacitor 124 having a first displacement capacitor 126 (referred to as a +Z-axis sensor) formed by first and second sensing capacitors 126a and 126b, and a second displacement capacitor 128 (referred to as a −Z-axis sensor) formed by third and fourth sensing capacitors 128a and 128b. Second micromachined comb drive 130 includes an actuation capacitor 132 (referred to as an X-axis actuator) formed by a first actuation capacitor 132a (referred to as a +X-axis actuator) and a second actuation capacitor 132b (referred to as a −X-axis actuator), and a displacement sensor capacitor 134 having a first displacement capacitor 134a (referred to as a +X-axis sensor) and a second displacement capacitor 134b (referred to as a −X-axis sensor). As will be described in greater detail below, each of the actuation and sensing capacitors is a comb-type capacitor having a number of overlapping fixed and moveable fingers or combs.

As will also be described in greater detail below, 2-D MEMS nanoindenter transducer 100 further includes four crash protectors 160, 162, 164, and 166 which are configured to restrict displacement of moveable probe 104 to prevent damage to the comb-type capacitors of comb drives 120 and 130 that might otherwise result from over-travel of the moveable fingers or combs.

As illustrated, 2-D MEMS nanoindenter transducer 100 has a length (L), a width (W), and a thickness (T). According to one embodiment, 2-D MEMS nanoindenter transducer 100 has a length (L) of 7.0 mm, a width (W) of 2.8 mm, and a thickness (T) of 0.30 mm, which dimensions are similar to those of the 1-D MEMS transducer, except that the 2-D MEMS nanoindenter transducer 100 is 50 µm thinner than the 1-D MEMS transducer. Since the outer dimensions of the 2-D MEMS nanoindenter transducer 100 are similar or slightly smaller than those of the 1-D transducer, the 2-D MEMS nanoindenter transducer 100 can be fitted within the same TEM holders employed with the 1-D transducer for mechanical testing. According to one embodiment, the thickness, T, (e.g. 0.30 mm) and the width, W, (e.g. 2.8 mm) are the dimensions critical for fitting the transducer into a TEM. For FEI TEMs, the maximum allowable thickness and width, which are restricted by the TEM pole gap and the geometry of the TEM holder, are 2.0 mm and 4.0 mm, respectively. The outer dimensions of the 2-D MEMS nanoindenter transducer 100 enable it to be fitted into such FEI TEMs.

According to one embodiment, in order to improve operational stability, 2-D MEMS nanoindenter transducer 100 employs a 0.1 mm×0.1 mm×1.5 mm indenter tip 205. By comparison, according to one embodiment, the 1-D transducer mounts a 0.2 mm×0.2 mm×1.8 mm indenter tip. The smaller dimensions of indenter tip 205 of 2-D MEMS nanoindenter transducer 100 increases its bandwidth in dynamic operation by reducing the mass of the moveable probe 104.

Figure 3:
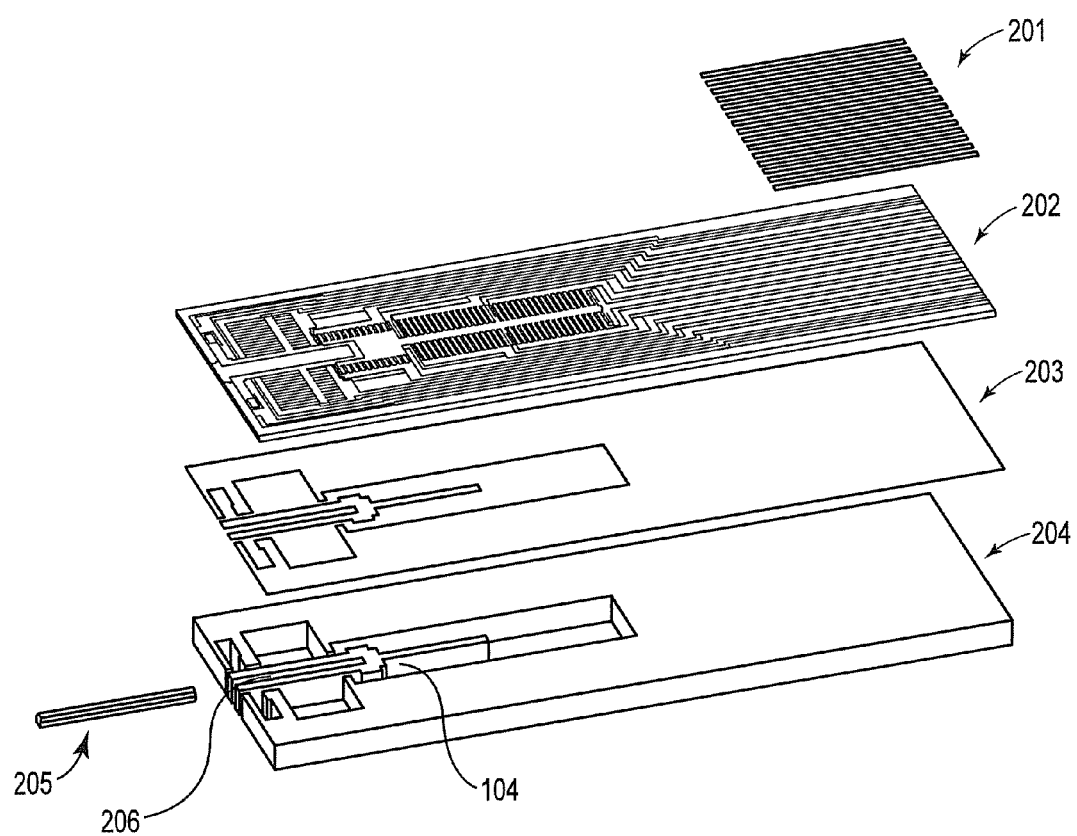
FIG. 3 is an exploded view of the 2-D MEMS nanoindenter transducer of FIG. 2, according to one embodiment.

FIG. 3 is an exploded view of 2-D MEMS nanoindenter transducer 100 of FIG. 1, according to one embodiment, including indenter tip 205. According to the embodiment of FIG. 2, body 102 of 2-D MEMS nanoindenter transducer 100 includes three layers, a metal layer 201, a device layer 202, and an oxide layer 203, on a substrate 204.

According to one embodiment, substrate 204 comprises p-type 100 silicon. According to one embodiment, substrate 204 has a thickness of 250 µm which is suitable to contain indenter tip 205 having a 100 µm diameter as well as several tens of microns thickness of an epoxy layer securing indent tip 205 to moveable probe 104.

Oxide layer 203 insulates device layer 202 from substrate 204. According to one embodiment, oxide layer 203 is a 1.5 µm oxide layer, which maintains parasitic capacitance at an acceptable level (e.g. 1 pf) and enables moderate fabrication costs.

According to one embodiment, first and second micromachined comb drives 120 and 130, springs 106, 108, 110, and 112, and crash protectors 160, 162, 164, and 166, are formed from device layer 202. According to one embodiment, device layer 202 comprises p-type (100) silicon. According to one embodiment, device layer 202 is 50 µm thick. According to one embodiment, the thickness of device layer 202 is determined based on the requirements of deep reactive ion etching (DRIE) fabrication processes. According to one embodiment, 6 µm features are formed on the device layer, wherein an aspect ratio of these features to the thickness of device layer 202 is 10:1, which enables the use of DRIE etching processes without large error. As will be describe in greater detail below, a plurality of electrodes are formed on device layer 202 to provide electrical pathways to the various devices such as indenter tip 205 and micromachined comb drives 120 and 130.

Metal layer 201 is deposited on device layer 202 and is employed for electrically connecting the electrical traces or electrodes of 2-D MEMS nanoindenter transducer 100 with an electrical circuit board (not shown), such as a printed circuit board (PCB). According to one embodiment, metal layer 201 comprises gold. Moveable probe 104 is formed from device, oxide, and substrate layers 202, 203, and 204.

According to one embodiment, 2-D MEMS nanoindenter transducer 100 is micromachined using silicon-on-insulator (SOI) wafers. According to one embodiment, in order to achieve a high electrical conductivity, heavily boron doped p-type silicon wafers were used for the device and substrate layers. According to one embodiment, a resistivity of the wafer was 0.005-0.02 ohm-cm. According to one embodiment, as described above, first and second micromachined comb drives 120 and 130 are fabricated using deep reactive ion etching (DRIE) techniques.

According to one embodiment, substrate layer 204 is deep etched to form a trench 206 configured to receive indenter tip 205. According to one embodiment, a thickness of substrate layer 204 is selected as necessary to contain indenter tip 205 as well as several tens of microns of an epoxy layer (not shown). According to one embodiment, indenter tip 205 comprises a diamond tip, for example. According to one embodiment, deep trench 206 is micromachined on substrate layer 204.

The deep and long trench 206 enables the mounting of an indenter tip, such as indenter tip 205, without damaging 2-D MEMS nanoindenter transducer 100. The long and narrow characteristics of mounting trench 206 help to align indenter tip 205 with Z-axis 114. According to one embodiment, trench 206 has an open side and a closed side, wherein the open side of mounting trench 206 enables epoxy to be applied after the mounting of indenter tip 205. According to one embodiment, indenter tip 205 is attached in mounting trench 206 using an epoxy. According to one embodiment, the indenter tip 205 is attached in mounting trench 206 using an electrically conductive epoxy.

A contact area between indenter tip 205 and moveable electrode 104 is electrically isolated from other portions of 2-D MEMS nanoindenter transducer 100, including micromachined comb drives 120 and 130. Such electrical isolation enables 2-D MEMS nanoindenter transducer 100 to be used for applications in electrical measurement and electron microscopy in-situ testing. Electrical measurement during nanoindentation provides correlation between the electrical measurement change and nanoindentation. Electrically isolated conductive indenter tip 205 can also be used to discharge electrons for in-situ electron microscopy tests.

An electron charged indenter tip can cause a large attractive force and which can result in jump-to-contact. This attraction by the accumulated electrons is undesirable because it distorts the measurement data by adding the attraction to the indentation loading/unloading curve. Therefore, discharging the electrons by grounding the electrically isolated conductive tip improves the performance of 2-D MEMS nanoindenter transducer 100 for applications in in-situ electron microscopy testing.

Figure 4:
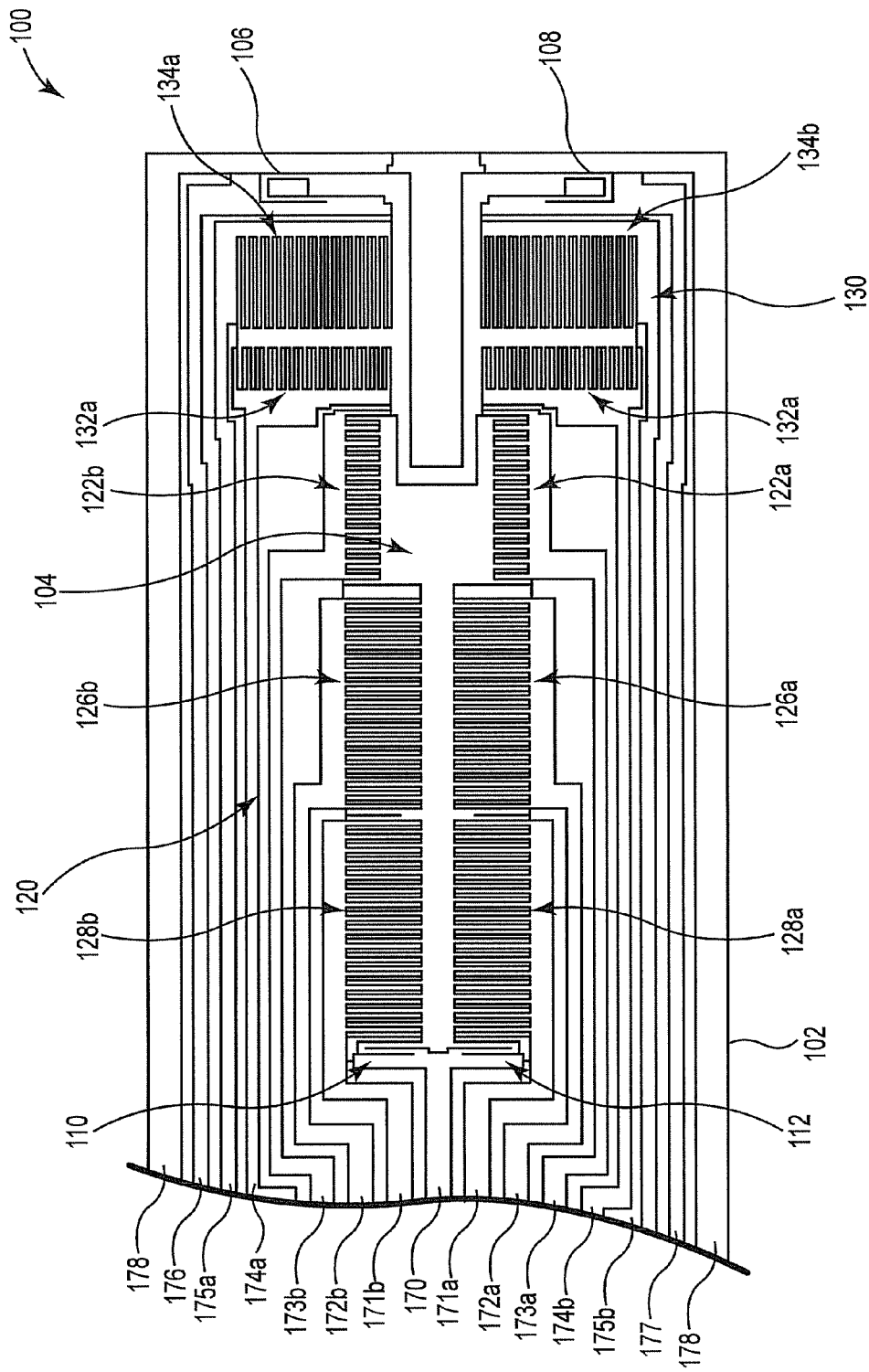
FIG. 4 is a top view of the 2-D MEMS nanoindenter transducer of FIG. 2, according to one embodiment.

FIG. 4 is a top view illustrating portions of 2-D MEMS nanoindenter transducer 100, according to one embodiment of the present disclosure. As shown in FIG. 4, and as will be illustrated in greater detail below by FIG. 5, each of the first and second Z-axis actuation capacitors 122a, 122b, first and second Z-axis sensing capacitors 126a, 126b, third and fourth Z-axis sensing capacitors 128a, 128b, first and second X-axis actuation capacitors 132a, 132b, and first and second X-axis sensing capacitors 134a, 134b include multiple pairs or sets of comb capacitors, with one comb of each pair of comb capacitors being a stationary of fixed electrode comb extending from body 102 and one moveable electrode comb extending from moveable probe 104.

According to one embodiment, as illustrated by FIG. 4, first and second Z-axis actuation capacitors 122a and 122b each have 12 electrode comb pairs such that Z-axis actuator 122 has a total of 24 electrode comb pairs for actuation of moveable probe 104 along the Z-axis 114, and first, second, third, and fourth sensing capacitors 126a, 126b, 128a, and 128b each have 13 electrode comb pairs such that Z-axis sensor capacitor 124 has a total of 64 electrode comb pairs for Z-axis differential displacement sensing of moveable probe 104. Also as illustrated by the embodiment of FIG. 4, +X-axis actuation capacitor 132a and −X-axis actuation capacitor 132b each having 13 electrode comb pairs so that X-axis actuation capacitor 132 has a total of 26 electrode comb pairs for lateral actuation of moveable probe 132 along X-axis 116, and +X-axis sensing capacitor 134a and −X-axis sensing capacitor 134b each have 14 electrode comb pairs so that X-axis displacement sensing capacitor 134 has a total of 28 electrode comb pairs for X-axis differential displacement sensing of moveable probe 104. According to one embodiment, as will be described in greater detail below by FIG. 5, each actuation electrode comb pair has an overlapping area of 130 μm×50 μm, and each displacement sensing electrode comb pair has an overlapping area of 330 μm×50 μm.

As further illustrated by FIG. 4, a plurality of electrodes are formed in device layer 202 to provide electrical pathways to the comb type capacitors of first (Z-axis) and second (X-axis) comb drives 120 and 130 and indenter tip 205. According to the embodiment of FIG. 4, electrode 170 extends to the moveable electrode combs of first, second, third, and fourth Z-axis sensing capacitors 126a, 126b, 128a, and 128b via springs 110, 112 and moveable probe 104; electrodes 171a and 171b extend to the fixed electrode combs of third and fourth Z-axis sensing capacitors 128a and 128b; electrodes 172a and 172b extend to the fixed electrode combs of first and second Z-axis sensing capacitors 126a and 126b; electrodes 173a and 173b extend to fixed electrode combs of first and second actuation capacitors 122a and 122b; electrodes 174a and 174b extend to the fixed electrode combs of X-axis actuating capacitors 132a and 132b; electrodes 175a and 175b extend to the fixed electrode combs of X-axis sensing capacitors 134a and 134b, electrode 176 extends to the moveable electrode combs of first and second X-axis actuating capacitors 132a, 132b and of first and second X-axis sensing capacitors 134a, 134b via spring 106 and moveable probe 104; electrode 177 extends to indenter tip 205 via spring 108 and moveable probe 104, and electrodes 178 serve as ground connections. According to one embodiment, with reference to FIG. 3, the electrodes are separated from one another by trenches penetrating through the 50 μm thickness of device layer 202.

Figure 5:
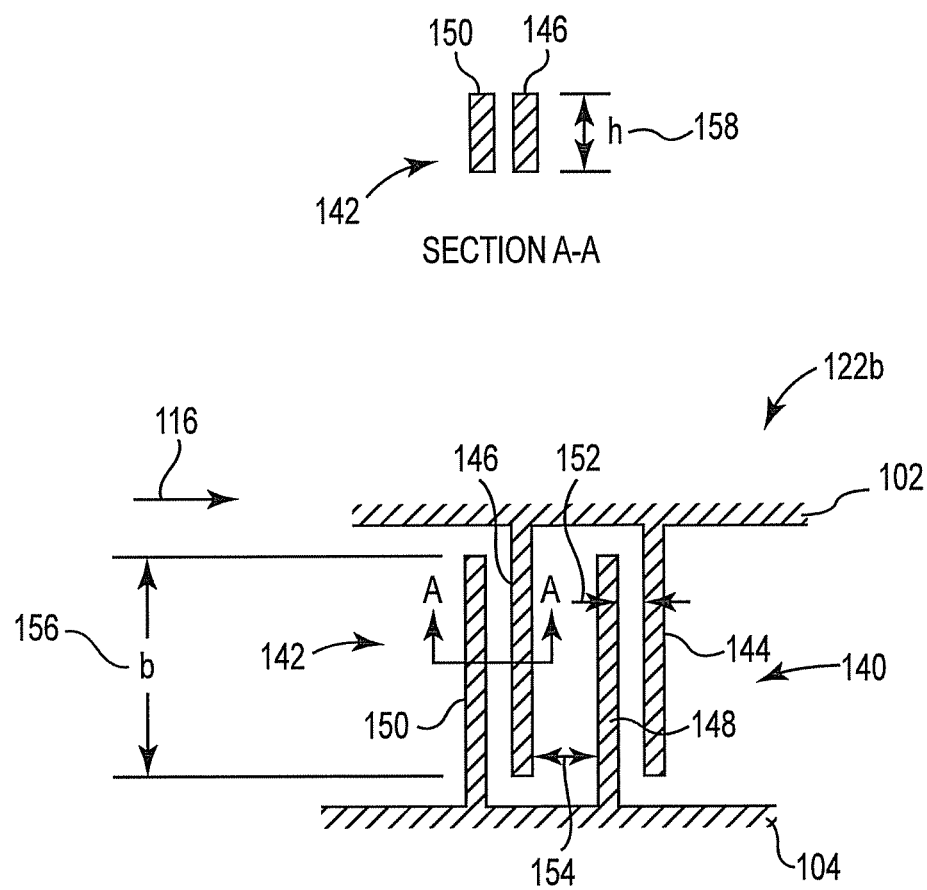
FIG. 5 illustrates two set of electrostatic actuator combs according to one embodiment.

FIG. 5 is a diagram generally illustrating two sets of electrostatic actuation comb capacitors 140 and 142 of Z-axis actuation capacitor 122b of comb drive 120, according to one embodiment. While actuation capacitor 122b includes more than two sets of actuation comb capacitors (see FIG. 4 above), for ease of illustration, only two sets of actuation comb capacitors (i.e. 140 and 142) are shown in FIG. 5. While described with respect to actuation capacitor 122b, it is noted that following discussion applies to Z-axis actuation capacitor 122a and X-axis actuation capacitors 132a and 132b as well.

Electrostatic actuation comb capacitors 140 and 142 respectively include fixed electrode combs 144 and 146 extending from body 102 and movable electrode combs 148 and 150 extending from a lateral edge of and moveable with moveable probe 104. According to one embodiment, a small gap, as illustrated by gap 152 between fixed electrode comb 144 and movable electrode comb 148 has a gap distance three times smaller than larger gap 154 between movable electrode comb 148 and fixed electrode comb 146. According to one embodiment, when fixed electrode comb 144 and moveable electrode comb 148 are biased, an electrostatic force in smaller gap 152 becomes 9 times greater than that in larger gap 154, thereby creating a differential force which pulls movable probe 104 in indentation direction 116. According to one embodiment, gap 152 has a gap distance of approximately 10 μm and gap 154 has a gap distance of approximately 30 μm.

In FIG. 5, an overlapping width, b, between the fixed and moveable electrode combs is illustrated at 156. Additionally, a section A-A through electrostatic actuation capacitor 142 illustrates, as indicated at 158, an overlapping height, h, between fixed and moveable electrode combs 146 and 150.

It is noted that actuation comb capacitors 140 and 142 are illustrated in their "home" or "zero" positions when actuation comb capacitors 140 and 142 are unbiased and MEMS nanoindenter transducer 100 is not engaging a test sample. As such, according to one embodiment, as illustrated by FIG. 5, large gap 154 has a gap distance which is three times greater than small gap 152 (i.e. the moveable electrodes are not disposed at equal distances between fixed electrodes).

As mentioned above, to actuate or displace moveable probe 104 and indenter tip 205 in indentation direction 116, a bias voltage is applied to the electrostatic actuation comb capacitors of actuation capacitor 122b (as well as to those of actuation capacitor 122a) to generate an electrostatic force between the fixed and moveable electrodes, such as between fixed and moveable electrode combs 144 and 148. The electrostatic force displaces moveable probe 104 in indentation direction 116 against a countering force from springs 106, 108, 110, and 112 which attempt to maintain moveable probe 104 in the so-called home position. According to one embodiment, a bias voltage is applied to fixed electrodes combs, such as fixed electrode combs 144 and 146, while the corresponding moveable electrode combs, such as moveable electrode combs 148 and 150 are at a fixed voltage relative to the bias voltage, such as at ground, for example.

Actuation capacitor 122b employs an electrostatic force generated by a change in capacitance of each set of electrostatic actuation comb capacitors (e.g. electrostatic actuation comb capacitors 140 and 142 of FIG. 4) resulting from an applied bias voltage. The capacitance of actuation capacitor 122b can be changed by changing a gap between the fixed and moveable electrode combs or by changing an overlapping area of the fixed and moveable electrode combs (e.g. fixed and moveable electrode combs 144 and 148 of FIG. 4). For a gap changing operation, an electrostatic force generated between two electrode combs, such as fixed and moveable electrode combs 144 and 148, can be represented by Equation I as follows:

$$F_d = \frac{\varepsilon b h}{2 d^2} V^2;$$

where the $F_d$ is the electrostatic force to the gap changing direction, $\varepsilon$ is the dielectric permittivity, b represents an overlapping width of the electrodes (see FIG. 4), h is an overlapping height of the electrodes (see FIG. 4), d is the gap between electrodes (see FIG. 4), and V is the applied or bias voltage.

According to one embodiment, with reference to FIG. 3 above, the electrode combs of the actuation and sensing comb capacitors of micromachined comb drives 120 and 130 are electrically isolated by deep trenches formed so as to penetrate through the device layer 202. According to one embodiment, with reference to FIG. 4 below, in order to adjust an overlapping area between plates or electrodes of the comb-type capacitor of actuation capacitor 120 and sensing capacitors 130, 132, 134, and 136, a thickness of device layer 202 may be adjusted. For example, to increase the overlapping area, the thickness of device layer 202 may be increased.

According to one embodiment, the actuation capacitors 122 and 132 of micromachined comb drives 120 and 130 can be operated according to a gap closing scheme, as described above, or according to an overlapping area change scheme (also referred to as lateral operation). When operated accord to a gap closing scheme, actuation capacitors 122 and 132 can generate a relatively large force by making a large capacitance change with respect to the gap change, but have a travel range which is relatively small due to the limited gaps between the electrode combs. Conversely, an overlapping area change scheme may have a large travel range since travel is not limited by an electrode gap, but does not provide as large a force as compared to a gap closing actuation scheme. It is noted that nanoindentation applications do not require a large travel range (e.g. a 1 µm displacement), but do require a large indentation force (e.g. up to 500 µN). As such, according to one embodiment, 2-D MEMS nanoindenter transducer 100 employs a gap closing scheme as described above.

According to one embodiment, 2-D MEMS nanoindenter transducer 100, as described above, employs a normal or Z-axis electrostatic actuation capacitor 122 (formed by first and second actuation capacitors 122a and 122b), and a lateral or X-axis electrostatic actuation capacitor 132 (formed by first and second actuation capacitors 132a and 132b). According to one embodiment, a maximum indentation force (i.e. along Z-axis 114 in indentation direction 116) provided by actuation capacitor 122 has been estimated at 552 µN, which is approximately half the maximum indentation force provided by the 1-D transducer. According to one embodiment, a maximum lateral force provided to each side of moveable probe 104 by first and second X-axis actuation capacitors 132a, 132b is estimated at 229 µN. This lateral force enables 2-D MEMS nanoindenter transducer 100 to measure a large friction coefficient even when the maximum indentation force is applied.

According to one embodiment, as will be described in greater detail below (see FIG. 12), 2-D MEMS nanoindenter transducer 100 is operated near a null tip position (indenter tip remains stationary relative to body 102 with moveable probe 104 kept in the "home" position) using a closed loop feedback control scheme so that a large travel distance is not required. According to one embodiment, a travel limit of 2-D MEMS nanoindenter transducer 100 is restricted within 1 µm by software control (see FIGS. 1 and 12).

FIG. 6 shows a Table I illustrating a detailed performance description of electrostatic actuating capacitor 122 providing normal actuation or movement along Z-axis 114 via actuating capacitors 122a, 122b, and electrostatic actuating capacitor 132 providing lateral actuation or movement along X-axis 115 via actuating capacitors 132a, 132b. In Table I, breakdown voltages at the nominal gap were estimated using Paschen's law, which describes the breakdown voltage as a function of a gap and the pressure. The estimated values are for a case in an ambient condition, which could be higher when the 2-D MEMS nanoindenter 100 is operated in a high vacuum. The maximum electrostatic forces are estimated for a case when 300V, which is close to the breakdown voltage, is applied. With respect to the travel limit, it is noted that movement of the 104 is physically limited via crash protectors.

According to one embodiment, as will be described below with respect to FIG. 7, a differential capacitive sensing scheme is employed to measure the indent or normal displacement of moveable probe 104 and indenter tip 205 along Z-axis 114 and the lateral displacement along X-axis 115. The motion of moveable electrode 104 corresponds with a capacitance change between stationary or fixed electrode combs extending from body 102 and moveable electrode combs extending from moveable probe 104. In general, a change in displacement from the null or home position of moveable probe 104 is measured from the signal output of sensor electronics which is proportional to the capacitance ratio between the moveable electrode combs and stationary electrode combs.

Figure 7:
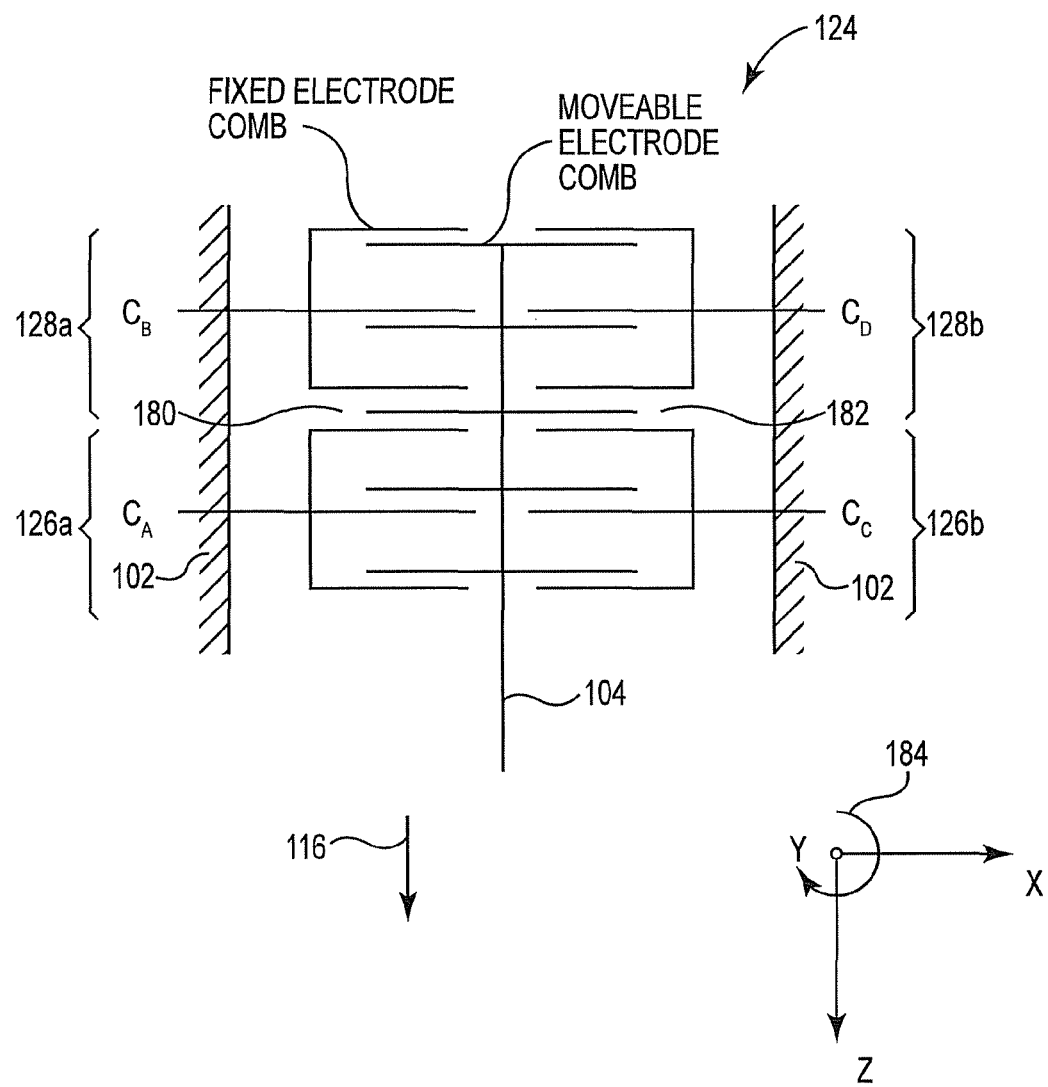
FIG. 7 illustrates a differential capacitance sensing scheme for sensing capacitors according to one embodiment.

FIG. 7 is a schematic diagram generally illustrating the configuration and electrical operation of sensing capacitors 126a, 126b, 128a, and 128b of sensing capacitor 124 of micromachined comb drive 120, according to one embodiment. Similar to electrostatic actuation comb capacitors 122a and 122b of actuation capacitor 122 of micromachined comb drive 120, as illustrated above by FIG. 5, sensing capacitors 126a, 126b, 128a, and 128b each include a plurality of sets of fixed and moveable electrode combs. While described with respect to Z-axis sensing capacitors 126a, 126b, 128a, and 128b of sensing capacitor of micromachined 124 of micromachined comb drive 120, it is noted that following discussion applies to X-axis sensing capacitor 134a and 134b of X-axis sensing capacitor 134 of micromachined comb drive 130 as well.

For ease of illustration, each of the sensing capacitors 126a, 126b, 128a, and 128b is shown in FIG. 6 as having only 3 sets of comb capacitors (rather than 13 sets as shown in FIG. 4), with each set having a fixed electrode coupled to body 102 and a moveable electrode coupled to and displaceable together with moveable probe 104. In FIG. 6, it is noted that a moveable electrode 180 is shared by sensing capacitors 126a and 128a, and that a moveable electrode 182 is shared by sensing capacitors 126b and 128b.

According to one embodiment, 2-D MEMS nanoindenter transducer 100 employs a differential capacitive sensing scheme to detect and measure displacement of movable probe 104. When moveable probe 104 is displaced, such as from application of a bias voltage to the fixed electrode combs of actuation capacitor 120, gaps between the fixed electrode combs and the moveable electrode combs of each of the sensing capacitors 126a, 126b, 128a, and 128b change which, in turn, changes the capacitance of each of the sensing capacitors 126a, 126b, 128a, and 128b.

The capacitance of each of the sensing capacitors 126a, 126b, 128a, and 128b in FIG. 6 (i.e. the sum of the capacitance of each of electrode comb pairs) are respectively represented as $C_A$, $C_B$, $C_C$, and $C_D$. It is noted that capacitance values $C_A$, $C_B$, $C_C$, and $C_D$ are electrical signals 50 representative of the capacitive values $C_A$, $C_B$, $C_C$, and $C_D$ provided to detection circuit 54 (see FIG. 1). Based on changes in the values of capacitances $C_A$, $C_B$, $C_C$, and $C_D$ relative to known reference values for these capacitances when moveable probe 104 is an unbiased state and not engaging a test sample (i.e. moveable probe is at a "home" position), the displacement of moveable electrode 104 in the indentation direction 116 (i.e.

z-axis), in the lateral direction (x-axis), and rotation of moveable electrode 104 about the y-axis can be determined.

Displacement of moveable electrode 104 in indentation direction 116 is determined based on a capacitance combination ratio ($CCR_I$) expressed by Equation II as follows:

$$CCR_I = \{(C_A + C_D) - (C_B + C_C)\} / \{(C_A + C_D) + (C_B + C_C)\}.$$

When moveable electrode 104 is moved in indentation direction 116, the sum of $(C_A + C_D)$ increases while the sum of $(C_B + C_C)$ decreases, resulting in an increase in $\{(C_A + C_C) - (C_B + C_C)\}$. Consequently, the value of $CCR_I$ increases relative to a reference value for $CCR_I$, determined using the known reference values for $C_A$, $C_B$, $C_C$, and $C_D$, by an amount that is proportional to the displacement of moveable probe 104 in indentation direction 116 (i.e. z-axis).

Displacement of moveable electrode 104 in the lateral direction (i.e. along the x-axis) is determined based on a capacitive combination ratio ($CCR_L$) expressed by Equation III as follows:

$$CCR_L = \{(C_A + C_B) - (C_C + C_D)\} / \{(C_A + C_B) + (C_C + C_D)\}.$$

When moveable probe 104 moves in the lateral direction (i.e. x-axis) the moveable electrode combs of sensing capacitors 126a, 126b, 128a, 128b move laterally relative to the fixed electrode combs so that the sum of $(C_A + C_B)$ increases while the sum of $(C_C + C_D)$ decreases due to a change in the overlapping area of the fixed and moveable electrode combs, resulting in an increase in $\{(C_A + C_B) - (C_C + C_D)\}$. Consequently, the value of $CCR_L$ increases relative to a reference value for $CCR_L$, determined using the known reference values for $C_A$, $C_B$, $C_C$, and $C_D$, by an amount that is proportional to the displacement of moveable probe 104 in the lateral direction (i.e. x-axis).

Rotation movement of moveable electrode 104 about the y-axis, as indicated at 184, is determined based on a capacitive combination ratio (CCRR) expressed by Equation IV as follows:

$$CCR_R = \{(C_B + C_D) - (C_A + C_C)\} / \{(C_B + C_D) + (C_A + C_C)\}.$$

When moveable probe 104 rotates in a clockwise direction, the sum of $(C_B + C_D)$ increases while the sum of $(C_A + C_C)$ decreases due to the rotational motion, resulting in an increase in $\{(C_B + C_D) - (C_A + C_C)\}$. Consequently, the value of $CCR_R$ increases relative to a reference value for $CCR_R$, determined using the known reference values for $C_A$, $C_B$, $C_C$, and $C_D$, by an amount that is proportional to the angular rotation of moveable probe 104.

Unlike a simple two-electrode capacitive sensor, the differential capacitive sensor as described above provides a more accurate displacement measurement regardless of environment changes such as temperature and humidity variations. This provides great advantage of utilizing the differential sensing scheme for the applications in nano-scale measurement in a variety of environmental conditions.

FIG. 8 shows a Table II illustrating detailed performance information of normal or Z-axis displacement capacitors 126a, 126b, 128a, and 128b of first micromachined comb drive 120 and of lateral or X-axis displacement capacitors 132a, 132b of second micromachined comb drive 130. It is noted that a parasitic capacitance of 1 pF was used to estimate the non-linear behavior of the displacement sensing capacitors.

As described above, 2-D MEMS nanoindenter transducer 100 is configured to detect both Z- and X-axis motion of moveable probe 104. As described above, since moveable probe 104 will be operated at a null or home position, displacement sensing capacitors 126a, 126b, 128a, 128b, 132a, and 132b do not require a long-range linearity. This enables the gaps between electrode comb pairs to be reduced, thereby increasing displacement sensing sensitivity of the displacement sensing capacitors 126a, 126b, 128a, 128b, 132a, and 132b. According to one embodiment, 2-D MEMS nanoindenter transducer 100 employs a gap distance between electrode combs of sensing capacitors 126a, 126b, 128a, 128b, 132a, and 132b of 6 µm. This gap is smaller than the gap distance of 10 µm employed by one embodiment of the 1-D MEMS transducer. Accordingly, the displacement sensitivity, which is actually a capacitance gradient to the operational direction, shows that the normal or Z-direction will be 3 times more sensitive than that of the 1-D MEMS transducer whose sensitivity is 10 fF/µm. According to one embodiment, lateral motion displacement sensing is 50% more sensitive than that of normal motion sensing of the 1-D MEMS transducer. Such sensitivity values are proportional to displacement scale factors (displacement versus signal output from the detection circuit) of each displacement sensor. The high sensitivity of 2-D MEMS nanoindenter transducer 100 is achieved using the smaller gap distance of 6 µm as compared to the 10 µm gap distance between electrode combs of the 1-D MEMS transducer.

Figure 9:
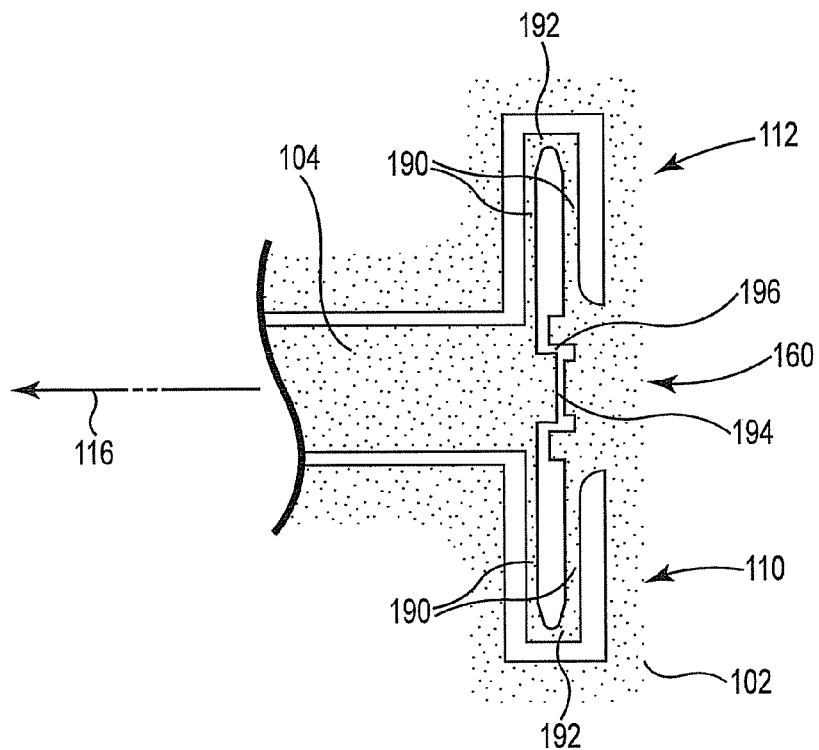
FIG. 9 is a diagram illustrating a spring and a crash protector according to one embodiment.

FIG. 9 is a diagram generally illustrating rear springs 110 and 112 and crash protector 160 proximate to the rear springs, according to one embodiment. According to one embodiment, as illustrated by springs 110 and 112, each of the springs 106, 108, 110, and 112 have a greater stiffness to displacement in the lateral directions (X-axis and Y-axis) as compared to a stiffness to displacement in indentation direction 116 (Z-axis). Accordingly, each spring has thin, long segments 190 in the lateral direction along the x-axis, and a thick, short segment 192 in indentation direction 116. Such a spring design substantially limits dislocation of indenter tip 205 of moveable probe 104 from displacement axis 114 in the x and y directions which might otherwise occur due to friction during an indentation procedure. Such spring characteristic is important for in-situ TEM nano-indentation especially when a sample surface is not perpendicular to the indentation direction.

As noted above, crash protectors prevent contact from occurring between the fixed and moveable electrode combs of micromachined comb drives 120 and 130 which might otherwise occur due to misoperation or mishandling and which could result in permanent damage to the transducer and controller electronics. As mentioned above, according to one embodiment, crash protectors 160, 162, 164, and 166 are fabricated in device layer 202 (see FIG. 3).

According to one embodiment, as illustrated by crash protector 160 in FIG. 9, a gap 194 is formed along the z-axis (i.e. in the direction of the displacement axis 114, see FIG. 2) between body 102 and moveable probe 104, and a gap 196 is formed along the x-axis (lateral direction) between body 102 and moveable probe 104. According to one embodiment, gaps 194 and 196 have a gap distance which is less than a gap distance between the fixed and moveable electrode combs of actuation capacitor 120 and sensing capacitors 130, 132, 134, and 136 (e.g. gap 152 as shown in FIG. 4). According to one embodiment, the crash protectors 160, 162, 164, and 166 limit the movement of moveable electrode 104 to 3 µm, which is less than the smallest electrode comb pair gap of 6 µm such that a "crash" cannot occur between the fixed and moveable electrode combs. It is noted that contact between crash protectors does not electrically impact the transducer as the contacting portions of the crash protector are of the same electrode.

Static characteristics of 2-D MEMS nanoindenter transducer 100 were evaluated using finite element analysis. According to one embodiment, the stiffness to normal (Z-axis) and lateral (X-axis) movement was determined to be approximately 200 N/m. Such a stiffness value is desirable based on experience with the 1-D transducer. Too large a spring stiffness will reduce force sensitivity. Additionally, too low of a spring stiffness reduces fabrication yield resulting from over-etching to produce too thin of a spring.

FIG. 10 shows a Table III illustrating detailed static characteristics of 2-D MEMS transducer 100, according to one embodiment. It is noted that lateral stiffness was estimated based on displacement of indenter tip 205, not moveable probe 104, and an applied force at indenter tip 205. The stiffness in the lateral direction varies depending on the length of indenter tip 205. The value illustrated in Table III represents an arrangement where indenter tip 205 extends from moveable probe 104 by 0.5 mm.

According one embodiment, a stress analysis of springs 106, 108, 110, and 112 was performed with moveable probe 104 displaced by 1 μm along Z-axis 114 in the displacement direction 116. The maximum stress with 1 μm Normal motion on rear springs 110 and 112 was determined to be 24 MPa. For lateral motion of 1 μm along X-axis 115, the maximum stress on front springs 106 and 108 was determined to be 20 MPa. Such stresses are far lower than the yield strength of a single crystal silicon (e.g. 100), which is 7 GPa. Such low stresses indicate that, with a 1 μm motion range, 2-D MEMS transducer 100 will not be damaged or have any plastic deformation and enables the springs to maintain linearity with the elastic deformation.

Dynamic characteristics of MEMS nanoindenter transducer 100 were also investigated using finite element analysis. According to one embodiment, the resonance frequency of 2-D MEMS nanoindenter transducer 100 to the normal (Z-axis) direction was determined to be 3.2 kHz. The corresponding dynamic mode is the translational oscillation to the normal direction. According to one embodiment, the resonance frequency to the lateral direction was determined to be 4.1 kHz. The corresponding dynamic mode is the rotational oscillation to the lateral direction.

Such resonance frequencies are higher than other known commercial non-MEMS tribometers which commonly have resonance frequencies lower than 1 k Hz. These high resonance frequencies are achieved by using a lower mass for the normal translation mode and a lower moment-of-inertia for the lateral rotational mode while having comparable stiffness. This high resonance frequency or high transducer bandwidth contributes to faster settling and better controllability. The settling time is inversely proportional to the resonance frequency and can be expressed as $$t_s \approx \frac{Q}{f_n},$$

where $t_s$ is the settling time, Q is the system quality factor, and $f_n$ is the resonance frequency. As described by the equation, the high resonance frequency makes the settling time shorter.

Figure 12:
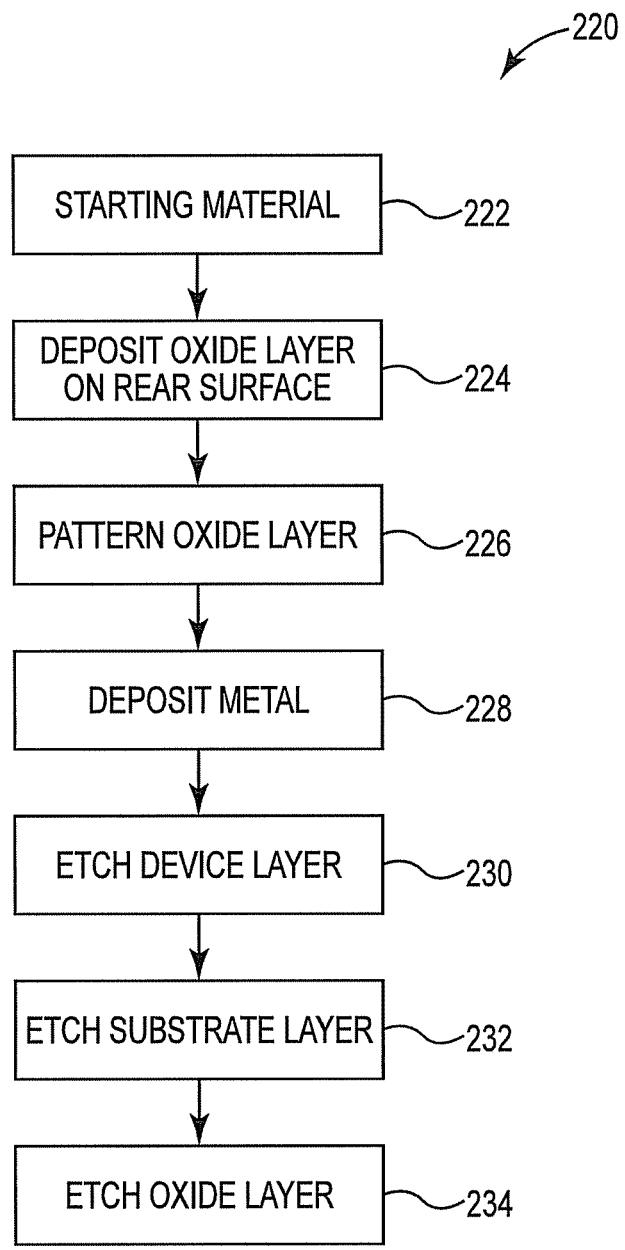
FIG. 12 is a flow diagram generally illustrating a process for fabrication of a 2-D MEMS nanoindenter transducer, according to one embodiment.

According to one embodiment, as will be described in greater detail below with reference to FIG. 12, the 2-D MEMS tribometer 100 is configured to operate with closed loop feedback control regulating indenter tip 250 at the null position. In this operation, the tracking error in the closed loop control is added to the measurement error. Having a higher bandwidth and better control is important in operation to reduce the measurement error caused by control tracking error.

FIG. 11 shows a Table IV detailing dynamic characteristics of 2-D MEMS transducer 100, according to one embodiment. It is noted that the mechanical quality factors are assumed values made based on the dynamic measurements of the 1-D MEMS transducer.

According to one embodiment, a displacement distribution was determined when a 100 μN friction force and a 138 μN balancing force (wherein the differential lateral sensor 134 is zeroed with this balancing force) were applied to 2-D MEMS nanoindenter transducer 100. The estimated result showed that when the lateral displacement sensor 134 is balanced (i.e. when the sensor is reading zero), indenter tip 250 has a 13 nm displacement. Such a discrepancy between the lateral displacement sensor 134 and the actual motion of indenter tip 205 is cause by the moment applied to indenter tip 205 with the friction and the balancing force (the control effort). This 13 nm displacement results in a 2.1 μN friction overestimation (2.1% friction coefficient measurement error) by adding spring force to the friction estimation.

Rotating a TEM holder enables users to investigate a test sample with different view angles which provide more interesting and clear material structural shapes and behaviors. Although such rotation along the primary axis (alpha-tilt) is useful for material research, this can cause performance degradation by the movable electrode displacement due to the gravity. This problem is more serious for probes having heavy movable parts and large gravity-caused displacement.

The 2-D MEMS tribometer is advantageous for such alpha-tilt operation because it has low mass and small gravity-caused displacement. According to one embodiment, the total estimated mass of the movable electrode including the indenter tip is 0.5 mg. With a 30 degree alpha-tilt, the gravity on the tribometer moves the tip about 10 nm to X-axis. To pull it back to the null tip position, the X-axis actuator needs to apply only a 2.4 μN balancing force. This 2.4 μN balancing force is less than 1% of the maximum X-axis force 299 μN.

Figure 13:
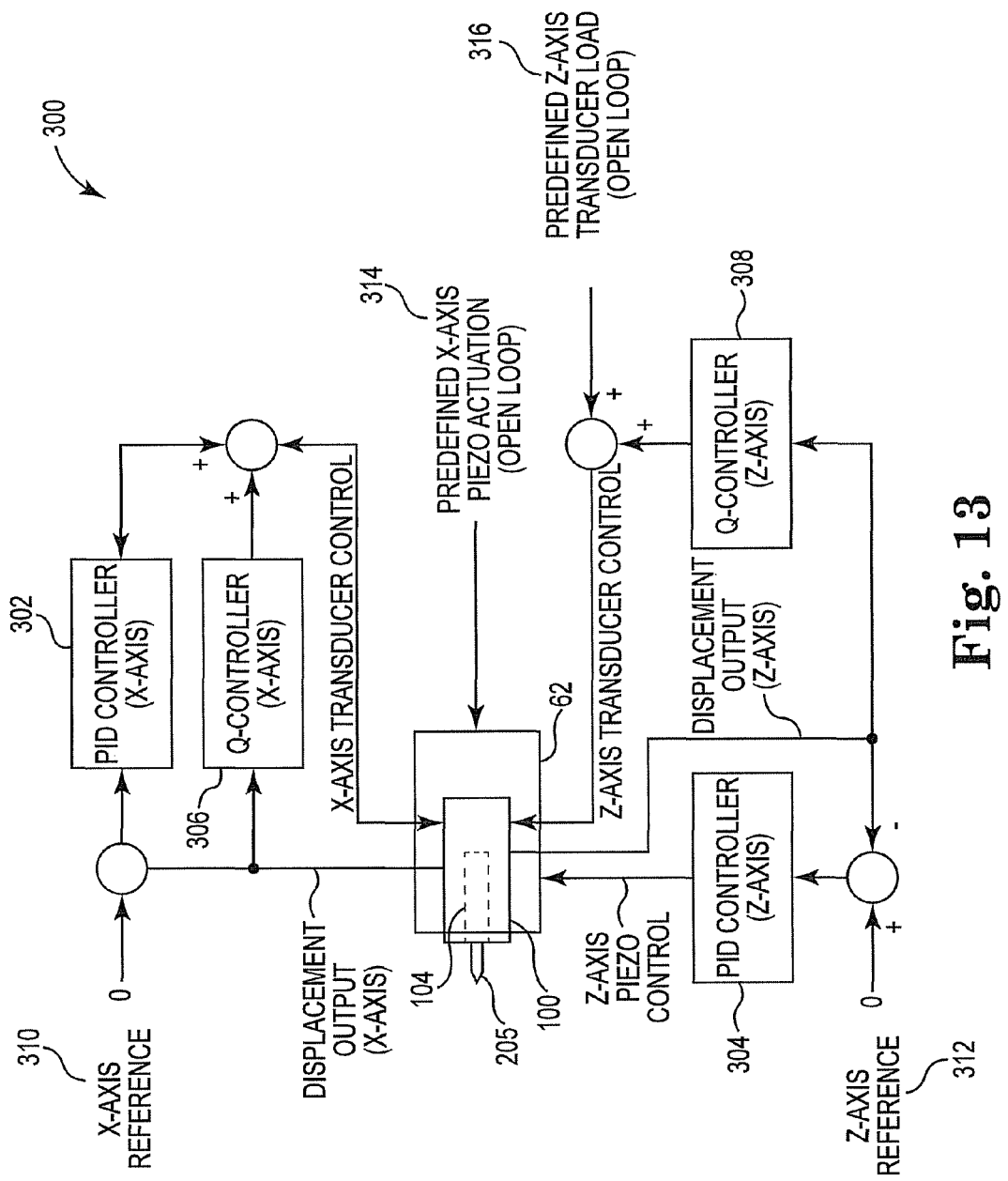
FIG. 13 is a schematic diagram of a control scheme according to one embodiment.

FIG. 13 is a process flow diagram generally illustrating one embodiment of a process 220 of fabrication of 2-D MEMS nanoindenter transducer 100 using silicon micromachining techniques. Process 220 begins at 222 with a starting material. According to one embodiment, the starting material comprises a silicon-on-insulator (SOI) wafer. According to one embodiment, as described above, heavily boron doped p-type silicon wafers were used for device and substrate layers 202 and 204 in order to achieve a high electrical conductivity. According to one embodiment, a resistivity of the wafer ranges from 0.005-0.02 ohm-cm.

At 224, an oxide is deposited on the rear or back side of substrate layer 204. At 226, the oxide deposited at 224 is opened, such as via reactive ion etching (RIE), using a mask (e.g. photoresist) having a pattern including the desired shape and dimensions of moveable probe 104.

At 228, metal is deposited on device layer 202, followed at 230 by formation of a mask having a desired pattern and etching of device layer 202 via deep reactive ion etching (DRIE). At 232, substrate layer 204 is etched (e.g. DRIE) via the patterned oxide on the back side thereof. At 234, the oxide layer deposited at 224 is removed and insulator layer 203 is etched via previously etched substrate layer 204.

FIG. 13 is a schematic diagram generally illustrating a closed-loop control scheme 300, according to one embodiment, for operating 2-D MEMS nanoindenter transducer 100 using a feedback control mode which regulates and maintains indenter tip 205 at the null or home position during a nano-tribology test. According to one embodiment, as illustrated, closed-loop control scheme 300 includes X- and Z-axis PID (proporational integral derivative) controllers 302 and 304, and X- and Z-axis Q-controllers 306 and 308.

According to one embodiment, to maintain the null position of indenter tip 205, both the X- and Z-axes are regulated at the balanced position by the closed loop control with zero reference inputs 310 and 312. According to one embodiment, a predefined X-axis piezo actuation, as indicated at 314, moves indenter tip laterally (i.e. X-axis) with the open loop operation. During piezo actuation, the position of indenter tip 205 is regulated at zero by doing PID control, via PID controller 302, with the X-axis actuator 132 and the X-axis displacement sensor 134 (see FIG. 2).

According to one embodiment, Q-control is implemented to suppress tip vibration caused by low damping inside a TEM. Q-control is a digital damping control algorithm which increases the system damping by three orders. An example of such Q-control suitable for use with the 2-D MEMS nanoindenter transducer 100 is described by U.S. patent application Ser. No. 12/498,238, assigned to the same assignee as the present application, and which is incorporated herein by reference. According to one embodiment, the Q-control algorithm can be integrated utilizing a phase shifting transfer function which provides frequency-dependent variable-time-delay to the output signal. The phase shifted signal is added to the system input with an appropriate gain. The system damping is manipulated by adjusting the damping controller gain. Clear evidence of the damping control and better vibration control inside a TEM has been observed from damping controlled responses. The implemented Q-control can effectively manipulate system damping in various environments. This damping control also works stably as a subsystem in the PID control.

According to one embodiment, Z-axis displacement regulation at zero position is performed by a z-axis piezo actuator closed loop control. A predefined Z-axis transducer load 216 is applied during the tribological test as the normal force. Q-control to suppress Z-axis vibration is also performed. For a scratch test of sample (e.g. sample 36 in FIG. 1), the compared value of the X-axis transducer force, which is equivalent to the lateral force, and the Z-axis transducer force, which is equivalent to the normal force, will provide the friction coefficient value. Since the force applied to the 2-D MEMS tribometer is the same as the sample reaction (assuming no spring force is applied at the null position), the transducer force will be recorded as the sample reaction to the Z-axis and X-axis. According to one embodiment, as illustrated, the two Q-controllers 208 and 208 are implemented to the two different directions and are operated simultaneously. This simultaneous Q-controller operation is possible because the vibration modes to those directions and operations are independent and are not coupled with each other.

According to one embodiment, a calibration setup is built using Hysitron's nano-indent system and comprises a stepping motor, a piezo-scanner, a transducer, and their controller electronics and driving software. Instead of vertical operation, which is the most common nano-indentation operation scheme, the system is modified for horizontal operation to make a room for TEM holder placing. According to one embodiment, the 2-D MEMS tribometer is calibrated by pushing the indenter tip with a reference transducer. According to one embodiment, the reference transducer comprises a laser-interferometer-calibrated nanoDMA transducer. By sustaining the tip with two center plates, when it is operated horizontally, the nanoDMA transducer has better stability than transducers having only one center plate. According to one embodiment, a 1-mm diameter sapphire tip is mounted on the DMA transducer to increase the feasible contact area and minimize the calibration error by the indenter penetration.

According to one embodiment, the TEM holder is mounted on a 3-axis micro-manipulator and the 2-D MEMS tribometer is coarsely approached to the reference transducer with the manipulator. According to one embodiment, once the 2-D MEMS tribometer tip is positioned within a 1-mm distance from the tip of the reference transducer (e.g. a sapphire tip) an automatic approach mechanism (e.g. Hysitron's automatic approach mechanism) is executed. Hysitron's automatic approach mechanism can make the tip contact safely with a contact force of only a few micro-newtons. After making the contact, the reference transducer actuates the 2-D MEMS tribometer. The sensor outputs from both transducers is then recorded. Both the normal and lateral direction displacement sensors and stiffness can be calibrated this way. The 2-D MEMS tribometer is highly suitable for such calibration because it is relatively insensitive to environmental noise and it has small mass and small gravity-induced displacement.

In summary, a micromachined 2-D MEMS nanoindenter transducer employing a micromachined comb drive is described, such as 2-D MEMS nanoindenter transducer 100 employing micromachined comb drive 119 (see FIG. 2). The MEMS nanoindenter transducer described by the present disclosure can be used in electron microscopy as well as ambient conditions. All the requirements as a nanoindenter and also in-situ TEM nano-mechanical tester were considered through the design and fabrication and the developed MEMS nanoindenter transducer satisfies required specifications such as physical dimensions, maximum force, spring stiffness, force sensitivity, dynamic bandwidth, travel range, and material restrictions. Experimental results with the MEMS nanoindenter transducer and Hysitron's instruments showed excellent instrument compatibility and versatile mechanical testing capabilities. Indentation, topography scanning, and dynamic testing capabilities were proven from the repeatable and robust nanoindenter operations. The MEMS nanoindenter transducer 100 can also be physically integrated into a variety of TEM holders and expands quantitative in-situ TEM nano-mechanical testing application to various TEMs which has been hindered by large transducer size. It is noted that a MEMS nanoindenter transducer according to the present disclosure, such as 2-D MEMS nanoindenter transducer 100, can also be incorporated into an SEM (scanning electron microscope) for in-situ mechanical testing applications.

In addition to these applications, a 2-D MEMS nanoindenter transducer according to the present disclosure can be applied to a variety of applications by integration into various instruments. For example, with its high bandwidth dynamic characteristic, the MEMS nanoindenter transducer can be used for high speed imaging and high speed modulus mapping. The high bandwidth characteristic also provides high frequency DMA testing capability. The low damping characteristic with high mechanical quality factor makes the dynamic responses sensitive to the sample interaction when the MEMS nanoindenter transducer is operated near the resonance frequency and can be used for topography measurement without damaging the sample surface. This is especially advantageous to increase the accuracy in measuring the indent on soft samples.

Another possible application is in-situ electrical measurement. The separated electrode line for the tip can be used to measure the electrical characteristic while doing indentation. In addition to the applications in quantitative in-situ mechanical testing, by utilizing its small size, the MEMS nanoindenter transducer can be integrated with various precision instruments, such as miniature manipulators, and can do mechanical property inspections and surface modifications in a small space.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A microelectromechanical (MEMS) nanoindenter transducer comprising:
   a body;
   a probe coupled to and moveable relative to the body, the probe holding a removeable indenter tip;
   a first micromachined comb drive including:
      an actuator comprising a plurality of electrostatic capacitive actuators configured to drive the probe along a first axis, including in an indentation direction, in response to an applied bias voltage; and
      a displacement sensor comprising a plurality of differential capacitive sensors having capacitance levels which together are representative of a position of the probe relative to the first axis; and
   a second micromachined comb drive including:
      an actuator comprising a plurality of electrostatic capacitive actuators configured to drive the probe along a second axis, which is perpendicular to the first axis, in response to an applied bias voltage; and
      a displacement sensor comprising a plurality of differential capacitive sensors having capacitance levels which together are representative of a position of the probe relative to the second axis,
   wherein each of the electrostatic capacitive actuators and each of the differential capacitive sensors comprises an electrode comb pair, each electrode comb pair including a fixed electrode comb coupled to the body and a moveable electrode comb coupled to the probe.

2. The MEMS nanoindenter transducer of claim 1, wherein the probe is coupled to the body by a plurality of deflectable springs.

3. The MEMS nanoindenter transducer of claim 2, wherein the springs maintain the probe at a null position when the actuators of the first and second micromachined comb drives are in an unbiased condition and the indenter tip is disengaged from an external test surface.

4. The MEMS nanoindenter transducer of claim 2, wherein the springs provide a stiffness against movement along the first axis which is less than a stiffness against movement in directions perpendicular to the first axis, including along the second axis.

5. The MEMS nanoindenter transducer of claim 1, wherein the actuator of the first micromachined comb drive comprises a first actuation capacitor and a second actuation capacitor disposed opposite from one another along the first axis and on opposite sides of the probe, wherein the fixed electrode comb of each of the electrostatic capacitive actuators of the first and second actuation capacitors extends from the body and the moveable electrode comb of each of the electrostatic capacitive actuators of the first and second actuation capacitors extends from the probe.

6. The MEMS nanoindenter transducer of claim 1, wherein the displacement sensor of the first micromachined comb drive comprises a first pair of sensing capacitors disposed opposite from one another along the first axis and on opposite sides of the probe, and a second pair of sensing capacitors disposed opposite from one another along the first axis and on opposite sides of the probe, wherein the fixed electrode comb of each of the differential capacitive sensors of the first and second pairs of sensing capacitors extends from the body and the moveable electrode comb of each of the differential capacitive sensors of the first and second pairs of sensing capacitors extends from the probe.

7. The MEMS nanoindenter transducer of claim 6, wherein the first and second pairs of sensing capacitors together provide capacitive levels indicative of linear displacement of the probe along the first axis.

8. The MEMS nanoindenter transducer of claim 1, wherein the actuator of the second micromachined comb drive comprises a first actuation capacitor and a second actuation capacitor disposed along the second axis and on opposite sides of the probe, wherein the fixed electrode comb of each of the electrostatic capacitive actuators of the first and second actuation capacitors extends from the body and the moveable electrode comb of each of the electrostatic capacitive actuators of the first and second actuation capacitors extends from the probe.

9. The MEMS nanoindenter transducer of claim 8, wherein the actuator is configured to apply a force to the probe in a first direction along the second axis and in a second direction, opposite the first direction, along the second axis.

10. The MEMS nanoindenter transducer of claim 1, wherein the displacement sensor of the second micromachined comb drive comprises first and second of sensing capacitors disposed along the second axis and on opposite sides of the probe, wherein the fixed electrode comb of each of the differential capacitive sensors of the first and second sensing capacitors extends from the body and the moveable electrode comb of each of the differential capacitive sensors of the first and second pairs of sensing capacitors extends from the probe.

11. The MEMS nanoindenter transducer of claim 10, wherein the first and second sensing capacitors together provide capacitive levels indicative of linear displacement of the probe along the second axis.

12. The MEMS nanoindenter transducer of claim 1, wherein the indenter tip is electrically isolated from the probe.

13. A nanoindentation test system comprising:
   a holder for retaining a sample;
   a microelectromechanical (MEMS) nanoindenter transducer comprising:
      a body;
      a probe coupled to and moveable relative to the body, the probe holding a removeable indenter tip;
      a first micromachined comb drive including:
         an actuator comprising a plurality of electrostatic capacitive actuators configured to drive the probe along a first axis, including in an indentation direction, in response to an applied bias voltage; and
         a displacement sensor comprising a plurality of differential capacitive sensors having capacitance levels which together are representative of a position of the probe relative to the first axis;
      a second micromachined comb drive including:
         an actuator comprising a plurality of electrostatic capacitive actuators configured to drive the probe along a second axis, which is perpendicular to the first axis, in response to an applied bias voltage; and
         a displacement sensor comprising a plurality of differential capacitive sensors having capacitance levels which together are representative of a position of the probe relative to the second axis, wherein each of the electrostatic capacitive actuators and each of the differential capacitive sensors comprises an electrode comb pair, each electrode comb pair including a fixed electrode comb coupled to the body and a moveable electrode comb coupled to the probe; and a controller configured to drive the moveable probe, along with the indenter tip coupled thereto, along the first and second axes so as to provide a desired force to the sample with the indenter tip by applying bias voltages to the actuators of the first and second micromachined comb drives based on displacement signals provided by the displacement sensors of the first and second micromachined comb drives.

14. The nanoindentation test system of claim 13, wherein the nanoindentation test system comprises an in-situ transmission electron microscopy mechanical test system.

15. The nanoindentation test system of claim 13, wherein the controller employs Q-control and PID control to maintain the indenter tip at a null position during a nano-tribology test.

\* \* \* \* \*